United States Patent [19]

Micheli

[11] 4,204,606
[45] May 27, 1980

[54] TUBE AND STOPPER COMBINATION WITH VENTING STRUCTURE

[75] Inventor: Antoine Micheli, Geneva, Switzerland

[73] Assignee: DEMATEX Development & Investment Establishment, Vadux, Switzerland

[21] Appl. No.: 847,606

[22] Filed: Nov. 1, 1977

Related U.S. Application Data

[63] Continuation-in-part of Ser. No. 668,795, Mar. 19, 1976, Pat. No. 4,066,067.

[30] Foreign Application Priority Data

Mar. 21, 1975 [CH] Switzerland .................. 3634/75

[51] Int. Cl.² ............... A61B 10/00; B65D 41/20; B65D 51/16
[52] U.S. Cl. ............................ 215/307; 128/764
[58] Field of Search .......... 128/220, 763, 764, 765, 128/766; 215/247, 260, 262, 270, 307, DIG. 3

[56] References Cited

U.S. PATENT DOCUMENTS

| | | | |
|---|---|---|---|
| 3,901,402 | 8/1975 | Ayres | 215/307 X |
| 3,948,261 | 4/1976 | Steiner | 215/307 X |
| 4,076,142 | 2/1978 | Naz | 215/307 |

*Primary Examiner*—Richard T. Stouffer
*Attorney, Agent, or Firm*—Robert E. Burns; Emmanuel J. Lobato; Bruce L. Adams

[57] ABSTRACT

An evacuated blood-sampling tube has a stopper with a skirt which fits over the open end of the tube. The stopper can be displaced to a venting position, in which an axial groove in the skirt communicates the interior of the tube with the exterior, to facilitate processing of the tube sample, including pipetting, with the tube stoppered. The tube may have a bead which engages one annular groove in the stopper to provide a sealing fit and another annular groove in the stopper skirt to define the venting position.

20 Claims, 10 Drawing Figures

TUBE AND STOPPER COMBINATION WITH VENTING STRUCTURE

This application is a continuation-in-part of my copending application Ser. No. 668,795, now U.S. Pat. No. 4,066,067.

BACKGROUND OF THE INVENTION

The invention relates to stoppers for vial-type tubes, in particular tubes subjected to a controlled pressure, for example evacuated tubes of blood sampling systems.

A known blood sampling system comprises an evacuated tube closed by a stopper and an open-ended needle-holder tube slidably mounted on the tube or its stopper. This needle holder carries a hollow needle having one part protruding axially from the closed end of the holder for pricking into a vein, and another part extending axially within the holder, the latter part being encased in a loose, flexible cover or sleeve. To take a blood sample, the needle is pricked into a vein and the evacuated tube displaced until the needle pierces the stopper membrane, so that blood is sucked into the evacuated tube.

However, in practice conventional blood sampling systems are often difficult to use and have shortcomings that create health hazard conditions for laboratory staff and may alter the results of some blood determinations.

Conventional stoppers usually have a shank which penetrates inside the tube neck, the shank having an externally bevelled end which is hollow to facilitate entry into the tube. As a consequence, blood particles may aggregate in recesses in the shank and when, after centrifugation, the stopper is removed these trapped particles may fall down into the centrifuged sample and alter the result of certain blood determinations.

Also, when the stopper is removed, blood particles on the shank tend to be sprayed as an aerosol, as a result of the "bouncing" effect. This is one of the main ways in which virus or bacteria contaminate laboratory staff. Handling such a stopper which has a surface smeared with blood is thus not only an unpleasant operation, but involves health hazards.

Many problems inherent to traditional evacuated tubes stem from the fact that sealing is achieved solely by the pressure of the outside wall of the stopper against the inner surface of the tube. This single sealing means serves both to prevent escape of the liquid content (blood) and penetration of air from the exterior. Removing or inserting the stopper produces instantaneous drafts of air which contribute to the aerosol effect.

Moreover, once such a stopper has been removed from an evacuated tube and the vacuum is lost, when it is reinserted in the tube it tends to be ejected as a result of compression of air in the tube. It is thus not suitable for reinsertion as a permanent closure.

SUMMARY OF THE INVENTION

An object of the invention is to provide a new stopper and tube combination which obviates the stated disadvantages.

The invention therefore provides, in combination, a vial-type tube and a stopper, the tube comprising a neck having an open end. The stopper comprises a hollow generally cylindrical body of deformable material having a head including a sealing membrane for fitting over and closing the open end of the tube and an integral skirt extending from the head for sealably fitting over the neck of the tube. In the stopper, there is at least one axially-directed groove extending from the edge of the skirt at least partly along the inner surface of the skirt. The stopper is movable outwardly on the tube from a sealing position in which part of the inner wall of the skirt sealably fits around the outer wall of the tube neck, to a venting position in which the axially-directed groove communicates the interior of the tube with the exterior.

Only a limited and generally inaccessible part of the stopper, namely the sealing membrane—usually a central plug which has a flat surface—can contact blood in the tube. This plug downwardly protruding from the membrane acts as a tight sealing means for the liquid content. The inner wall of the skirt, which assumes the main part of the vacuum retention function, is protected from any seepage of the tube content and stays dry. Thus, the sealing function is provided by two separate means, the plug for liquids (blood), and the inner skirt wall for air. Other forms could be made, however, in which each of two sealing means could serve for both sealing functions (liquid content and air penetration from the exterior). Also, there are no unoccupied volumes or recesses in which blood can form deposits. And all the outside surface of the stopper, as well as the inside wall of the skirt, is totally isolated from the tube content and stays dry and clean. The fitting-over form of the skirt hence makes the stopper convenient to handle and safe.

The venting system eliminates the aforementioned bouncing effect when the stopper is removed, by balancing pressures before the stopper is removed. Removal of the stopper is thus easy and smooth and the spraying of blood particles in an aerosol is avoided. The venting system can also be used to facilitate initial fitting of the stopper and evacuation of the tube, by carrying out evacuation with the stopper already placed on the tube in the venting position.

In one embodiment, the tube neck has an outwardly protruding annular bead and the stopper skirt has at least one annular groove configured in cross section to receive therein this annular bead with a sealing fit. In this embodiment the stopper is, in the same way, movable outwardly, in relation to the tube, from a sealing position, in which the bead fits sealably in one such annular groove, to a venting position in which the axially-directed groove communicates the interior of the tube with the exterior.

The complementary configurations of the bead on the tube and the annular groove in the stopper enable the stopper to be reseated on the tube as a permanent closure after loss of vacuum. This is further facilitated by the venting system, and by the fact that, at most, the stopper plug can only slightly penetrate in the tube, so that air in the tube will not be appreciably compressed.

In use, after a blood sample has been sucked into the evacuated tube, aspiration of the sample from the tube is facilitated by placing the stopper in the venting position, i.e. without a need to remove the stopper and open the tube.

The fitting-over form of the stopper skirt also enables the stoppering of vials and tubes having a neck of a smaller diameter than is suitable for receiving a conventional plug-like stopper.

BRIEF DESCRIPTION OF THE DRAWINGS

Embodiments of the invention will now be described, by way of example, with reference to the accompanying schematic drawings, in which.

DESCRIPTION OF PREFERRED EMBODIMENTS

Figure 1:
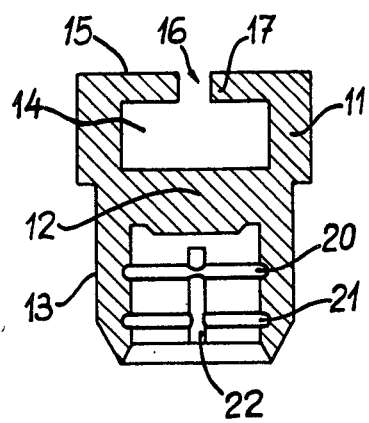
FIG. 1 is a cross-section of a first form of stopper.
Figure 2:
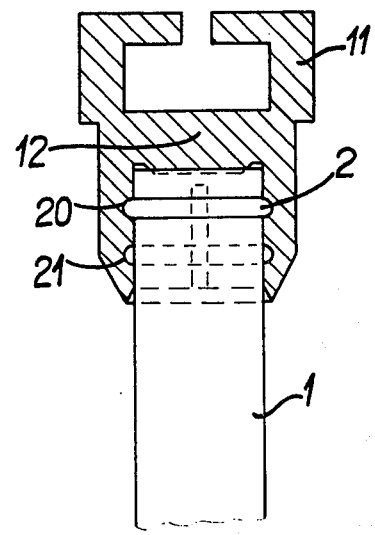
FIG. 2 shows the stopper of FIG. 1 fitted on a tube, in a pushed-in sealing position.

The stopper of FIGS. 1 and 2 consists of a hollow generally cylindrical body of deformable material, such as synthetic rubber, having a head 11 including a sealing membrane 12, and an integral skirt 13 extending from the head. The head 11 is hollow and has a chamber 14 with a flexible end wall 15 in which there is a central slot 16 defined between flexible radially-inwardly extending lips 17. Several stoppers with heads of this type are described in detail in copending application Ser. No. 668,795, and the head 11 may have the external form shown in FIG. 4, 7, 8 or 9 of said copending application.

The skirt 13 is adapted to fit over the end of a tube 1, as shown in FIG. 2, so that the membrane 12 closes the open end of the tube. The inner cylindrical face of skirt 13 has two annular grooves 20, 21 and an axially-directed groove 22, the grooves 20, 21 being able to receive an external annular bead 2 on the neck of tube 1. The axially-directed groove 22 is shallower than groove 20 which provides a sealing engagement; however, the axially-directed groove 22 is deeper than groove 21, so that when groove 21 engages on the bead 2, the groove 22 communicates the interior of tube 1 with the exterior.

To evacuate the tube 1, the stopper is placed in the venting position, i.e. with bead 2 engaged in groove 21, and the tube/stopper is placed in an evacuated enclosure having means for automatically pressing the stopper into the sealing position, i.e. with bead 2 engaged in groove 20, when a vacuum has been set up in the tube.

The evacuated tube may be used with a slidable needle-holder of the type mentioned at the outset, and shown in FIG. 1 of copending application Ser. No. 668,795, to take a blood sample. During blood sampling, the stopper of course remains in the sealing position. However, to remove the blood sample after centrifugation, the stopper is pulled out to the venting position. This allows air to enter the tube and then, by piercing the membrane 12 with a hollow probe or other pipetting device connected to an evacuating pump, the blood sample can be pipetted out of the tube without removing the stopper. Hence, processing of the tube sample, including pipetting out the content, can be done with the tube stoppered.

Handling of the tube/stopper assembly is facilitated and, even when the stopper is removed, is clean and hygienic since the blood can only contact the flat inner surface of membrane 12 which is shielded by the skirt 13.

Figure 3:
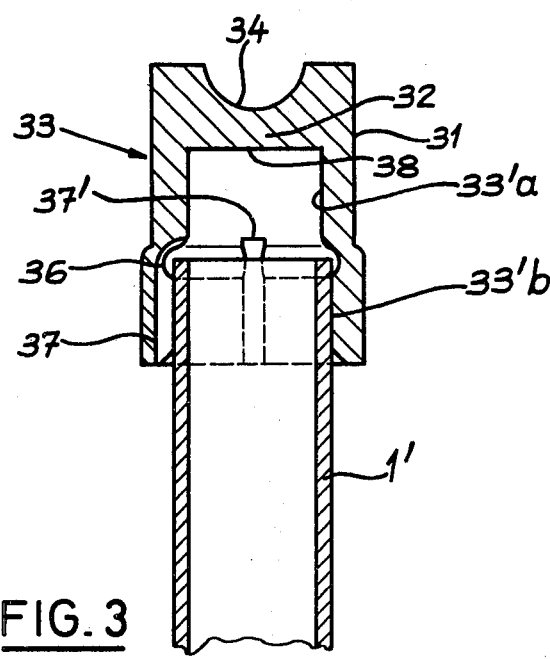
FIG. 3 is a cross-section of a second form of stopper fitted on a tube in a vented position.

FIG. 3 shows a tube and stopper combination of which the tube neck 1' has a smooth cylindrical outer surface, and the stopper consists of a head 31 and an integral skirt 33 extending flush from the generally cylindrical side wall of the head. A sealing membrane 32 is defined by a central dimple 34 in the head 31.

An annular interruption in the form of a groove 36 is provided in the skirt 33, approximately mid-way between the skirt edge and the closed end 38 of membrane 32, and axially directed grooves 37, 37' extend from the skirt edge, partly along the inner surface of skirt 33.

As shown, the axially-directed grooves 37, 37' are deeper than and intersect the annular groove 36. The annular groove 36 divides the skirt 33 into two cylindrical portions, an upper one 33'a extending to the closed end 38 and a lower one 33'b extending to the skirt edge. The axially-directed grooves 37, 37' extend only slightly into the inner surface of the upper portion 33'a which, otherwise, is smooth and uninterrupted. When the tube neck 1' is introduced into the lower portion 33'b of the stopper skirt, the annular groove 36 prevents the outward deformation of portion 33'b from being totally transferred to the upper cylindrical portion 33'a. The latter thus remains inset compared to the portion 33'b and forms, at the level of the annular groove 36, a stop against which the external rim of the tube rests to define a venting position in which the axially-directed grooves 37, 37' communicate the interior of the tube with the exterior. When the stopper is fully pushed on by applying a further force, the upper skirt portion 33'a also deforms outwardly to receive the tube neck with a tight sealing fit.

Figure 4B:
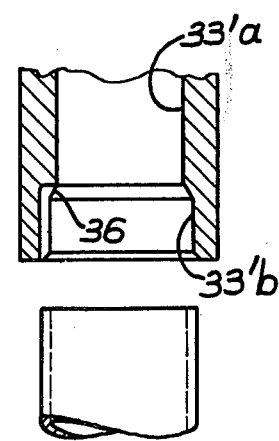
FIG. 4 shows a third form of stopper fitted on a tube in a pushed-in sealing position, the same stopper and tube being shown separated from one another in FIG. 4b.
Figure 4:
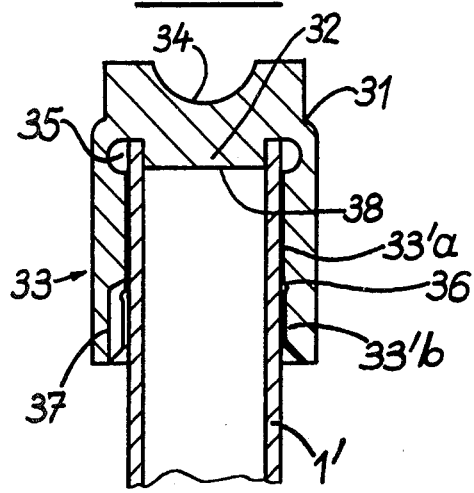

In the tube and stopper combination of FIG. 4, a tube 1' has a cylindrical outer surface, and the stopper has a head 31 with a dimple 34 defining a membrane 32 which includes a central plug 38 surrounded by an inwardly directed groove 35. As in FIG. 3, the skirt inner wall is split into two adjacent cylindrical portions, the upper one 33'a comprising, between the annular groove 35 and the top of axially-directed groove 37 a non-interrupted surface. The lower one 33'b has a slightly enlarged diameter, compared to adjacent upper portion 33'a, the two portions being connected by an annular interruption in the form of a slanted section 36 (shown in FIG. 4b). The inside diameter of portion 33'b, when unstressed, is slightly smaller than the outside diameter of the tube neck. The stopper can thus be pulled out from the sealing position shown in FIG. 4 until the portion 33'b elastically grips the end of the tube neck with the axially-directed groove 37 communicating the interior of the tube with the exterior. As the skirt 33 tends to elastically return to a diameter smaller than the outer diameter of the tube 1' the enlargement facilitates fitting of the stopper on the tube.

Figure 5:
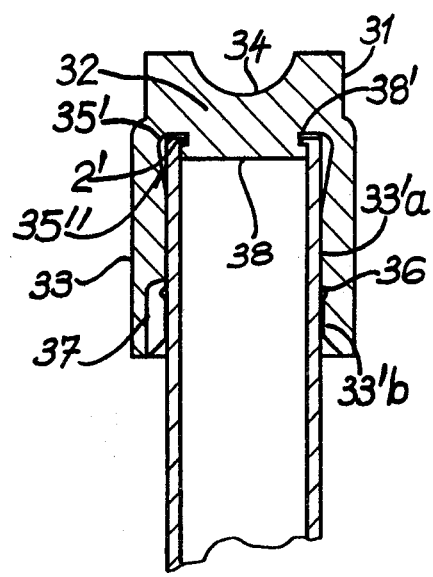
FIG. 5 shows a variation of the embodiment of FIG. 4 in which the tube has an inwardly directed rim.

FIG. 5 shows a variation of the tube stopper combination of FIG. 4. The tube 1' has a rim 2', slightly protruding as an inward bead, at the end of the neck. The stopper has an outwardly facing annular groove 38', inset in the periphery of plug 38 for sealably engaging with the rim 2'. Sealing is further improved by the sealing surface portion 33'a of the skirt 33 which tightly fits about the tube neck. The annular groove 35 of FIG. 4 is modified in FIG. 5 by being interrupted at its maximum diameter 35', the recess in the inner surface of the skirt 33 having a generally conical section 35" flaring outwardly from the sealing portion 33'a to 35'. All the other parts are unchanged and designated by same references as in FIG. 4.

Figure 6:
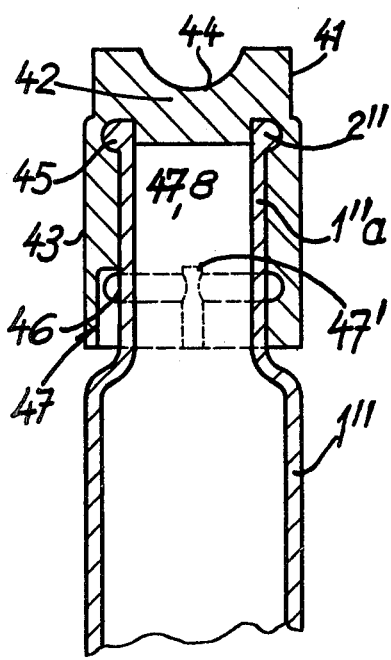
FIG. 6 is a cross-section of a fourth form of stopper fitted on a tube, in a pushed-in sealing position.
Figure 7:
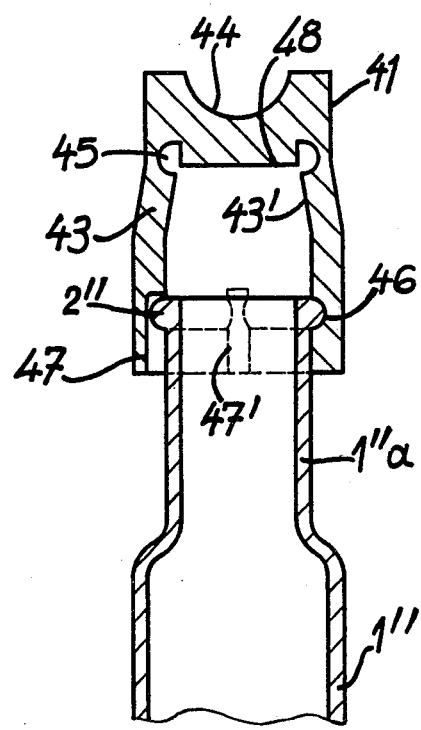
FIG. 7 shows the stopper and tube of FIG. 6, in a pulled-out venting position.

FIGS. 6 and 7 show a tube/stopper combination of which the stopper consists of a head 41 and an integral skirt 43 extending flush from the generally cylindrical side wall of the head. A sealing membrane 42 is defined by a central dimple 44 in the head 41. Membrane 42 includes a central inwardly-protruding plug 48 which is surrounded by a first inwardly-facing annular groove 45 in the end part of the skirt 43, adjacent head 41. A second annular groove 46 is provided in the skirt near its edge and axially-directed grooves 47, 47' extend from the edge of skirt 43, partly along the inner surface of the skirt which has a smooth uninterrupted surface portion 43' extending to the groove 45. As shown, the axially-directed grooves 47, 47' are deeper than and intersect the annular groove 46.

The annular grooves 45, 46 are each shaped in cross-section to receive an outwardly-projecting bead 2" forming a rim on the open end of the cylindrical neck 1"a of vial-like tube 1". The skirt 43 has approximately the same length as the neck 1"a and an outer diameter such that when the stopper is fully pushed on the tube neck 1"a, i.e. with the bead 2" located in groove 45, it is substantially flush with the enlarged cylindrical body of tube 1". In this position the bead 2" sealably fits in groove 45, and the portion 43' of the skirt closely circumferentially fits on the neck 1"a. Also, the plug 48 penetrates slightly into the open end of neck 1"a to improve sealing, especially as regards the escape of any liquid content of tube 1". When the stopper is pulled out until the bead 2" engages in groove 46, the axially-directed grooves 47, 47' communicate the inside of tube 1" with the exterior. The stopper/tube combination thus has discrete sealing and venting positions. As with the other embodiments, at no time does the inside of skirt 43 or its outer peripheral surface come into contact with the tube content.

Figures 8, 9:
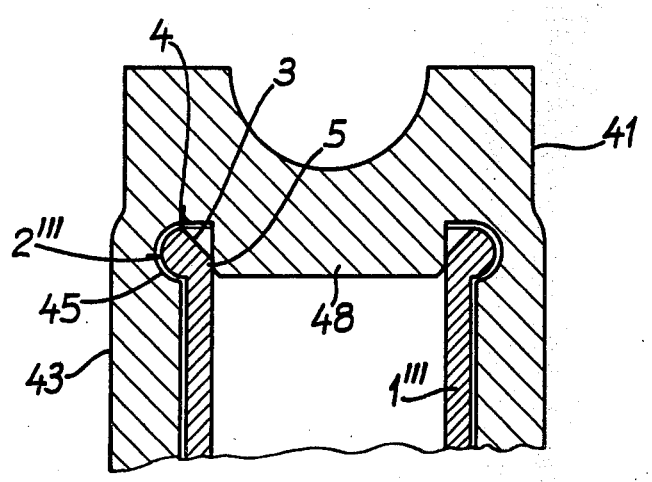
FIG. 8 shows a varied form of the stopper of FIGS. 6 and 7 in cross-section, and the neck of a tube in elevation.
FIG. 9 is a cross-section of part of a stopper similar to that of FIGS. 6 and 7 fitted on a modified tube, in a sealing position.

FIG. 8 shows a modified form of the stopper of FIGS. 6, 7 without a central plug 48 of the membrane 42 of head 41, and having a third annular groove 45' spaced apart from the groove 46 towards the edge of skirt 43. The axially-directed grooves 47, 47' intersect grooves 45' and 46; they are shallower than groove 45', and deeper than groove 46. Thus, with this embodiment, there is a pushed-in sealed position (bead 2" in groove 45), an intermediate venting position (bead 2" in groove 46) and a pulled-out sealed position (bead 2" in groove 45'). Of course, this stopper could also have a plug 48 as in FIGS. 6, 7 to improve sealing in the pushed-in position.

In FIG. 9, a stopper of the type shown in FIGS. 6 and 7 and identified by the same references cooperates with a tube 1''' whose cylindrical inner surface is extended, at the rim, by an outwardly-flaring trunco-conical surface 3 which terminates at the upper edge 4 of an outwardly-protruding curved external surface forming a bead 2''' on the rim. The plug 48 of stopper head 41 is dimensioned so that when the stopper is in the pushed-in sealing position with bead 2''' engaged in groove 45, the plug 48 sealably engages the cylindrical inner surface of tube 1''' at 5. In this position, a space is left between the cylindrical periphery of plug 48 and the trunco-conical surface 3. The plug 48 thus remains out of contact with the curved external surface of bead 2''' when the stopper is moved into and out of the sealing position. This avoids any blood being transferred from the end of the plug 48 onto the outside of the tube. Instead of being conical, the surface 3 could for example have a concave arcuate section.

Naturally, many variations may be made to the described embodiments, and features of one embodiment may be combined with another embodiment, where appropriate. Also, instead of an axially-directed groove, equivalent venting means could be provided for communicating the interior of the tube with the exterior when the stopper is held on the tube in a venting position. And the term "axially-directed" groove is intended to include grooves and similar recesses having a major axial component to provide the desired venting effect.

What is claimed is:

1. In combination, a vial-type tube and stopper, the tube comprising a neck having an open end, and the stopper comprising a hollow generally cylindrical body of deformable material having a head including a sealing membrane for fitting over and closing the open end of the tube and an integral skirt extending from the head for sealably fitting over the neck of the tube, and means defining in the stopper at least one axially-directed groove extending from the edge of the skirt at least partly along the inner surface of said skirt, said stopper being outwardly movable on the tube from a sealing position in which part of the inner wall of the skirt sealably fits around the outer wall of the tube neck to a venting position in which said axially-directed groove communicates the interior of the tube with the exterior.

2. Tube and stopper combination according to claim 1, in which the stopper comprises means defining in the inner surface of the skirt an annular interruption intersecting with said axially-directed groove whereby when the stopper is pulled out from the sealing position until the open end of the tube neck engages said annular interruption, the stopper is held in said venting position.

3. Tube and stopper combination according to claim 1, in which said sealing membrane of the stopper head includes a central protruding plug that sealably fits in the open end of the tube neck when the stopper is in said sealing position.

4. Tube and stopper combination according to claim 3, in which the stopper comprises an inwardly facing annular recess in the end part of the skirt surrounding said plug.

5. Tube and stopper combination according to claim 4, in which said inwardly-facing recess in the end part of the skirt extends downwardly further than the plug to a generally cylindrical smooth uninterrupted sealing portion of the skirt.

6. Tube and stopper combination according to claim 5, in which said axially-directed groove extends from the edge of the skirt partly along its inner surface to a generally cylindrical smooth uninterrupted sealing portion of the skirt, said recess in the inner surface of the skirt extending upwardly beyond the sealing portion as a generally conical section flaring outwardly from said sealing portion to a maximum diameter at a location facing the peripheral wall of said plug.

7. Tube and stopper combination according to claim 3, in which the tube neck has a smooth cylindrical outer surface and a rim protruding inwardly from the open end of the neck, said plug of the stopper having on its peripheral surface an outwardly facing groove configured in cross-section to sealably receive therein said inwardly-protruding rim of the tube neck when the stopper is in said sealing position.

8. Tube and stopper combination according to claim 1, in which the inner surface of the skirt comprises first and second cylindrical portions, a generally uninterrupted first sealing portion adjacent the head of the stopper, said first sealing portion at most being interrupted only partially by an end part of said axially-directed groove, and a second cylindrical portion of greater diameter than said first portion, said second portion extending from adjacent said first portion to the edge of the skirt and being interrupted by said axial groove.

9. Tube and stopper combination according to claim 8, in which said first and second cylindrical portions are separated by an annular interruption in the skirt.

10. Tube and stopper combination according to claim 1, in which the tube comprises an outwardly protruding annular bead on its neck and the stopper skirt comprises at least one annular groove configured in cross section to receive therein said annular bead on the neck of the tube to provide a sealing fit.

11. Tube and stopper combination according to claim 10, in which the stopper skirt comprises a second annular groove intersecting said at least one axially-directed groove, said at least one axially directed groove having a deeper section than said second annular groove at their intersection, said second annular groove being configured to receive said bead to hold the stopper in said venting position.

12. Tube and stopper combination according to claim 10, in which said at least one axially directed groove intersects at least one said annular groove, the axially-directed grooves having a shallower section than said one annular groove at their intersection.

13. Tube and stopper combination according to claim 10, in which the stopper comprises first, second and third annular grooves spaced apart from one another in the direction from the head to the edge of the skirt and configured in cross-section to receive therein said annular bead on the neck of the tube to hold the stopper respectively in a first sealing position, a second venting position and a third sealing position, said at least one axially-directed groove intersecting the second and third annular grooves and having, at the respective intersections, a section deeper than the second annular groove and a section shallower than the third annular groove.

14. Tube and stopper combination according to claim 10, in which the tube neck has a cylindrical inner surface extended at the open end by an outwardly flaring surface of generally trunco-conical shape which terminates adjacent an outwardly-protruding curved external surface of said bead, said plug of the stopper being dimensioned so that when the stopper is in said sealing position with said bead engaging in said annular groove, the plug sealably engages the cylindrical inner surface of the tube neck, the plug being shaped so that it remains out of contact with said curved external surface of said rim when the stopper is moved into and out of said sealing position.

15. Tube and stopper combination according to claim 10, in which one annular groove in the inner surface of the skirt cooperates with said annular bead on the tube neck when the stopper is in said sealing position, said skirt extending from said groove in a tight seal zone for sealably fitting over the neck of the tube.

16. Tube and stopper combination according to claim 10, in which said sealing membrane of the stopper head includes a central protruding plug that sealably fits in the open end of the tube neck when the stopper is in said sealing position.

17. Tube and stopper combination according to claim 1, in which the stopper skirt comprises at least one annular groove which intersects said at least one axially-directed groove, the axially-directed grooves having a deeper section than at least one said annular groove at their intersection.

18. Tube and stopper combination according to claim 1, in which the neck of the tube is cylindrical and extends from a generally cylindrical body of larger diameter than the neck, the skirt of the stopper having a length and outer diameter in relation to the neck and body of the tube whereby said skirt is substantially flush with said body of the tube when the stopper is fully pushed on the neck.

19. Tube and stopper combination according to claim 1, in which said axially-directed groove extends from the edge of the skirt partly along the inner surface of the skirt, the skirt having a smooth uninterrupted surface portion adjacent said axial groove.

20. In combination, a vial-type tube and stopper, the tube comprising a neck having an open end, and the stopper comprising a hollow generally cylindrical body of deformable material having a head including a sealing diaphragm for fitting over and closing the open end of the tube, and an integral skirt extending from the head for sealably fitting over the neck of the tube, said stopper being outwardly movable on the tube from a sealing position in which part of the inner wall of the skirt sealably fits around the outer wall of the tube neck to a venting position in which the stopper is held on the tube by engagement of an end part of said skirt on an end part of the tube neck, and venting means for communicating the interior of the tube with the exterior when the stopper is held on the tube in said venting position.

* * * * *